United States Patent [19]

Brois et al.

[11] 4,292,184

[45] Sep. 29, 1981

[54] THIO-BIS-(HYDROCARBON-BISOXAZO-LINES) AS OLEAGINOUS ADDITIVES FOR LUBRICANTS AND FUELS

[75] Inventors: Stanley J. Brois, Spring, Tex.; Antonio Gutierrez, Mercerville, N.J.

[73] Assignee: Exxon Research & Engineering Co., Florham Park, N.J.

[21] Appl. No.: 134,511

[22] Filed: Mar. 27, 1980

Related U.S. Application Data

[60] Continuation-in-part of Ser. No. 23,615, Mar. 26, 1979, abandoned, which is a continuation-in-part of Ser. No. 817,217, Jul. 20, 1977, Pat. No. 4,174,322, which is a division of Ser. No. 726,206, Sep. 24, 1976, Pat. No. 4,062,786.

[51] Int. Cl.$^3$ .................. C10M 1/38; C10L 1/24; C07D 263/14
[52] U.S. Cl. ..................... 252/46.3; 44/63; 44/76; 252/47.5; 252/389 R; 252/391; 542/413; 542/427; 548/238
[58] Field of Search ............ 252/46.3, 47.5, 51.5 A, 252/391, 389 R; 44/63, 76; 542/413, 427; 548/238

[56] References Cited

U.S. PATENT DOCUMENTS

| | | | |
|---|---|---|---|
| 2,725,382 | 11/1955 | Harman | 252/47.5 X |
| 3,039,961 | 6/1962 | Harker | 252/47.5 |
| 3,172,892 | 3/1965 | Lesuer | 252/51.5 A X |
| 3,211,653 | 10/1965 | O'Halloran | 252/47.5 X |
| 3,389,124 | 6/1968 | Sparks | 252/47.5 X |
| 4,035,309 | 7/1977 | Brois | 252/49.7 |
| 4,062,786 | 12/1977 | Brois et al. | 252/51.5 R |

FOREIGN PATENT DOCUMENTS

| | | |
|---|---|---|
| 809001 | 2/1959 | United Kingdom . |
| 984409 | 2/1965 | United Kingdom . |
| 1483681 | 8/1977 | United Kingdom . |
| 1483682 | 8/1977 | United Kingdom . |

*Primary Examiner*—Andrew Metz
*Attorney, Agent, or Firm*—R. A. Dexter; J. J. Mahon

[57] ABSTRACT

Thio-bis-(hydrocarbon-bisoxazolines) which are the reaction products of thio-bis-(hydrocarbon substituted dicarboxylic acid material), for example, thio-bis-(polyisobutenyl succinic anhydride), with 2,2-disubstituted-2-amino-1-alkanols, such as tris-(hydroxymethyl) amino-methane (THAM), and their derivatives are useful additives in oleaginous compositions, such as sludge dispersants for lubricating oil, or anticorrosion agents for fuels.

16 Claims, No Drawings

THIO-BIS-(HYDROCARBON-BISOXAZOLINES) AS OLEAGINOUS ADDITIVES FOR LUBRICANTS AND FUELS

CROSS-REFERENCE TO RELATED APPLICATIONS

This application is a continuation-in-part of Ser. No. 23,615, filed Mar. 26, 1979 now abandoned, which in turn is a continuation-in-part of Ser. No. 817,217 filed July 20, 1977, now U.S. Pat. No. 4,174,322, which in turn is a division of Ser. No. 726,206 filed Sept. 24, 1976, now U.S. Pat. No. 4,062,786.

The present invention concerns oil-soluble thio-bis-(hydrocarbon-bisoxazolines) and their analogs, their method of preparation and the utility of said oxazolines in hydrocarbon fuel and lubricating systems as highly stable anticorrosion agents and/or sludge dispersants.

During the past decade, ashless sludge dispersants have become increasingly important, primarily in improving the performance of lubricants and gasoline in keeping the engine clean of deposits, and permitting extended crankcase oil drain periods. Most commercial ashless dispersants fall into several general categories. In one category, a polyamine is linked to a long-chain hydrocarbon polymer, such as polyisobutylene, through a dicarboxylic acid material, such as succinic anhydride, by forming amide or imide linkages, such as described in U.S. Pat. No. 3,172,892.

United Kingdom Specification No. 809,001 teaches corrosion inhibitors comprising a multiple salt complex derived from the reaction product of hydrocarbyl-substituted dicarboxylic acids and hydroxy amines (including 2-amino-2-methyl-1,3-propanediol [AMPD]) and tris-hydroxymethylaminomethane (THAM) further complexed with mono- and polycarboxylic acids (see Examples 17–19). United Kingdom Specification No. 984,409 teaches ashless, amide/imide/ester type lubricant additives prepared by reacting an alkenyl succinic anhydride, said alkenyl group having 30 to 700 carbon atoms, with a hydroxy amine including THAM. German OS No. 2512201 teaches reacting long-chain hydrocarbon-substituted succinic anhydride with 2,2-disubstituted-2-amino-1-alkanol to produce mono- and bisoxazoline products. Thio-bis-(alkyl lactone oxazolines), useful as oleaginous additives, and chlorine-containing thio-bis-adducts of sulfur chlorides with octenyl succinic anhydride are disclosed in U.S. Pat. No. 4,062,786.

It has now been discovered that the dehydrochlorinated thio-bis-adducts or acylating agents obtained by the reaction of sulfur halides with hydrocarbyl-substituted dicarboxylic anhydrides or acids or esters can be further reacted with 2,2-disubstituted-2-amino 1-alkanols to form oxazolines.

The reaction of the thio-bis-adducts or acylating agents is carried out using 1 to 4, preferably 2 to 4 molar equivalents of the alkanol per molar equivalent of said adduct. The most preferred proportions comprise 4 moles of the alkanol per mole of said acylating agent thereby forming a thio-bis-(hydrocarbon-bis-oxazoline) having about 4 oxazoline groups per molecule. These oxazolines are highly stable additives with outstanding varnish inhibition. A preferred member of this novel class of additives can be represented by the formula:

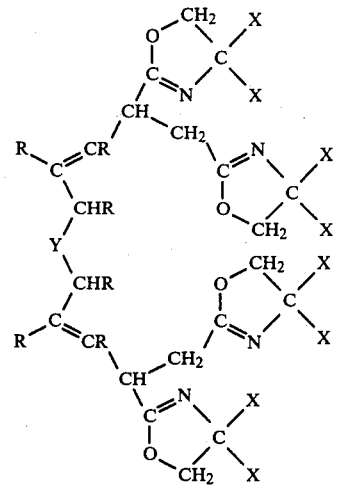

wherein R is selected from the group consisting of hydrogen and alkyl radicals containing from 1 to 400 carbons, X is selected from the group consisting of an alkyl or hydroxyalkyl group and at least one of the X substituents and preferably both of the X substituents being a hydroxy alkyl group of the structure $-(CH_2)_nOH$ where n is 1 to 3, and Y is selected from the group consisting of $-S-$, $-S-S-$, $>S=O$ (sulfinyl), $>SO_2$ (sulfonyl), $-Se-$ (seleno) and $-S-(CH_2)_z-S-$ wherein z is a number from 2 to 10.

Preferred herein is thio-bis-(polyisobutenyl-bisoxazoline) of number average molecular weight ranging from about 400 to 100,000 prepared by the reaction of thio-bis-(acylating reagent), e.g. thio-bis-(polyisobutenyl succinic anhydride), with tetramolar proportions of tris-(hydroxymethyl) amino-methane (hereinafter designated also as THAM). The reaction is carried out at a temperature from about 100° to 240° C., preferably 150°–180° C., until about six moles of $H_2O$ per mole of the thio reactant are removed from the reaction.

The novel compounds described above as effective detergents in lubricating oil compositions are also useful as detergents in fuel compositions, such as burner fuel compositions, and motor fuel compositions, for example, in gasolines and in diesel fuels.

The hydrocarbon-soluble compounds have at least 8 carbons in the aliphatic hydrocarbyl group of the thio-bis-(acylating reagent) converted into bisoxazoline rings as a result of the reaction of said thio-bis-(hydrocarbon substituted dicarboxylic acid material) and about tetramolar amounts of a 2,2-disubstituted-2-amino-1-alkanol having 1 to 3 hydroxy groups and containing a total of 4 to 8 carbons.

The preparation of the mono- or dithio-bis-(alkene dioic acid or anhydride or ester) or dithio-bis-(alkane dioic acid or anhydride or ester) acylating agents involve the sulfur halide coupling or bis-sulfenyl halide-induced coupling or the oxidative coupling of $H_2S$ or thioacid adducts of an olefin diacid. The olefin diacid material is readily obtained via the reaction of an olefin or a chlorinated olefin with an unsaturated $C_4$ to $C_{10}$ dicarboxylic acid, anhydride or ester thereof, such as fumaric acid, itaconic acid, maleic acid, maleic anhydride, dimethyl fumarate, etc. The dicarboxylic acid material formed via the Ene reaction of an olefin with maleic anhydride can be illustrated as an alkenyl-substituted anhydride which may contain a single alkenyl radical or a mixture of alkenyl radicals variously bonded to the cyclic succinic anhydride group, and is understood to comprise such structures as:

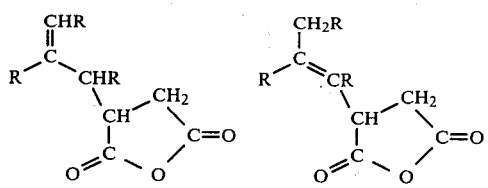

with the γ,δ-unsaturated isomers predominating and wherein R may be hydrogen or hydrocarbyl containing from 1 to about 400 carbons, preferably from about 16 to about 400 carbons and optimally from about 60 to about 100 carbons. The anhydrides can be obtained by well-known methods, such as the reaction between an olefin and maleic anhydride or halosuccinic anhydride or succinic ester. In branched olefins, particularly branched polyolefins, R may be hydrogen, methyl or a long-chain hydrocarbyl group. However, the exact structure may not always be ascertained and the various R groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups.

With 2-chloromaleic anhydride and related acylating agents, alkenylmaleic anhydride reactants are formed. Bridging of these products with $YCl_2$ also afford useful precursors. Preferred olefin polymers for reaction with the unsaturated dicarboxylic acids are olymers comprising a major molar amount of $C_2$–$C_5$ monoolefin, e.g., ethylene, propylene, butylene, isobutylene and pentene. The polymers can be homopolymers, such as polyisobutylene, as well as copolymers of two or more of such olefins such as copolymers of ethylene and propylene, butylene and isobutylene, propylene and isobutylene, etc.

The olefin polymers will usually have number average molecular weights ($\overline{M}_n$) within the range of 500 and about 140,000; more usually between about 700 and about 10,000. Particularly useful olefin polymers have ($\overline{M}_n$) within the range of about 700 and about 5,000 with approximately one terminal double bond per polymer chain. An especially valuable starting material for a highly potent dispersant additive are polyalkenes, e.g. polypropylene and polyisobutylene, having about 90 carbons.

The dicarboxylic acid materials (Diels-Alder adducts) formed via the reaction of a chlorinated olefin with maleic anhydride also useful in the present invention, can be illustrated in part, by the following structures:

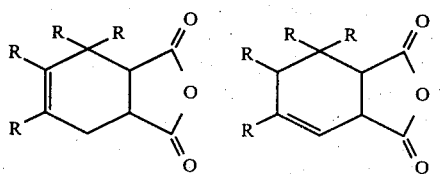

where R is as previously defined. Useful chlorinated olefins include chlorinated di-isobutylene, tri-isobutylene, polyisobutylene, tetrapropylene, polyisopropylene, and alkenes which upon halogenation characteristically gives allylic halide structures.

The bridging or coupling of the precursor acylating agents can be achieved by (i) addition of sulfur halides or bis-sulfenyl halides or alkyl sulfenate/HCl reagent to unsaturated diacid anhydrides, (ii) the oxidative coupling of unsaturated diacids or anhydrides or esters previously thiylated with $H_2S$ or $R_1C(=O)SH$, where $R_1$ represents a $C_1$–$C_5$ alkyl group, or (iii) reaction of α,ω-alkane-dithiols, $H_2S$, or a suitable thiylating agent, with epoxidized or halogenated alkene dioic acid or anhydride materials.

The preferred method to bridged acylating agents involves the reaction of sulfur halides, bis-sulfenyl halides or a sulfenate ester-HCl reagent with unsaturated diacid anhydrides in the temperature range of −60° C. to about 100° C., optimally from about 10° C. to 50° C. If desired, solvents comprising hydrocarbons, such as pentane, hexane, heptane, cyclohexane, mineral oil; halocarbons such as methylene chloride, chloroform, carbon tetrachloride, aromatics such as toluene, chlorobenzenes, xylene; ethers, such as diethyl ether and tetrahydrofuran(THF); and, acids such as acetic, propionic and trifluoroacetic acid, can be used in favorably controlling viscosity and reaction temperature. Usually, the sulfur halide is added dropwise to an unsaturated diacid anhydride, preferably diluted in an inert diluent. With reactive diluents and unsaturates such as polyisobutylene, sufficient sulfur halide must be added to effect complete bridging of the olefin diacid anhydride reactants.

When the addition of one mole of sulfenyl halide to 2 moles of alkene dioic acid anhydride is conducted at low temperatures, e.g. −60° C. to about 20° C., a discrete $YCl_2$-anhydride adduct forms which upon dehydrohalogenation gives a thio-bis-acylating agent as depicted in the equation:

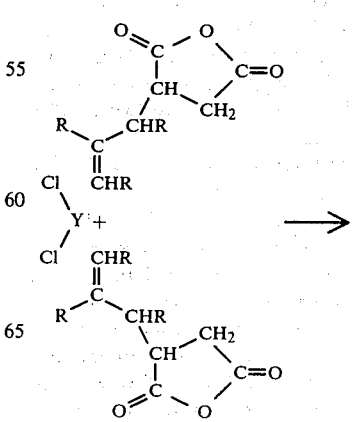

-continued

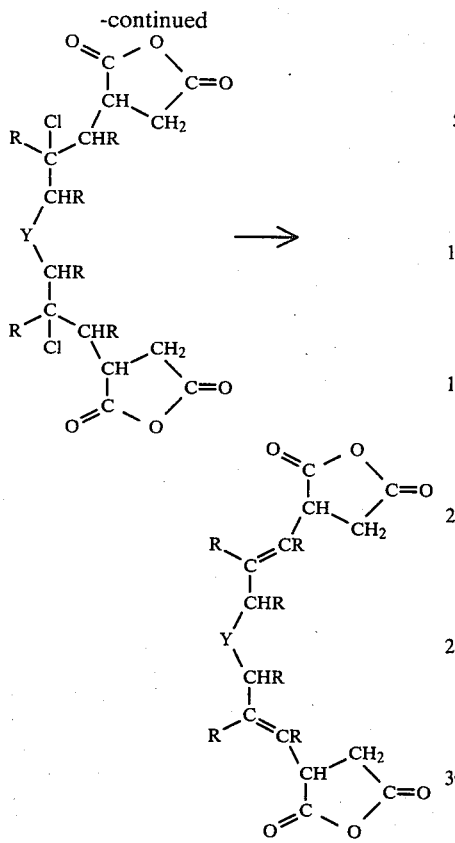

with R and Y being the same as previously defined.

Increasing the bridging temperature above about 50° C., and branching in the hydrocarbyl portion of the alkene dioic anhydride tend to accelerate the elimination of HCl from YCl$_2$-alkene dioic anhydride adduct. Since unsaturated bridged products can be further sulfenylated with YCl$_2$ reagent (re-addition), it becomes necessary in some cases, to modify the theoretical 2:1 stoichiometry to effect complete bridging. Accordingly, at higher temperatures, i.e. from 50°–100° C., ratios in the range of 1.5:1 to 1:1 may be required to realize higher conversions to bridged structures due to re-addition reactions, and the partial thermal decomposition of the sulfur halide reactant at elevated temperatures. While more sulfur halide reagent becomes necessary to achieve coupling, the additional sulfur incorporated into the dispersant precursor (and occasionally the diluent) tends to endow the resulting thioether products with enhanced oxidative stability.

As indicated above, sulfur halides including SCl$_2$, S$_2$Cl$_2$ and alkyl sulfenate ester/HCl reagent are suitable bridging agents. Bis-sulfenyl halides derived from alkane, heteroalkane, aromatic, heteroaromatic, and heterocyclic radicals such as

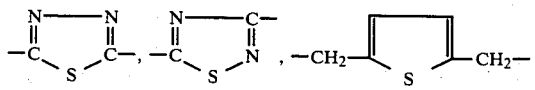

etc. are also useful coupling agents.

Oxidation of the monothio ether products provides access to useful sulfoxide and sulfone derivatives. A variety of inorganic and organic oxidizing agents can be used to effect these conversions including hydrogen peroxide, peracids, hydroperoxides, e.g. t-butyl hydroperoxide, chlorine, positive halogen reagents, nitric acid, oxides of nitrogen, oxygen, ozone and metal oxides. The preferred oxidant is hydrogen peroxide usually in acetic acid and as necessary in an aromatic solvent, e.g. toluene. Oxidation with equimolar quantities of reactants at about 0° to 60° C. provides the sulfoxide in excellent yield. A 2:1 molar ratio of peroxide to said thio ether product produces the sulfone derivative. The peroxide oxidation of sulfides to sulfones is preferably carried out in the presence of catalytic amounts of conventional oxidation catalysts such as tungsten, molybdenum, e.g. molybdenyl acetylacetonate, or vanadium salts.

The amino alcohol used to react with the thio-bis-(hydrocarbon substituted dicarboxylic acid material) is a 2,2-disubstituted-2-amino-1-alkanol containing a total of 4 to 8 carbon atoms, and which can be represented by the formula:

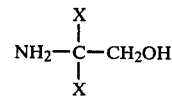

wherein X is an alkyl or hydroxy alkyl group, with at least one of the X substituents, and preferably both of the X substituents being a hydroxy alkyl group of the structure—(CH$_2$)$_n$OH, wherein n is 1 to 3.

Examples of such 2,2-disubstituted amino alkanols, include 2-amino-2-methyl-1,3-propanediol, 2-amino-2-(hydroxymethyl)-1,3-propanediol (also known as tris-hydroxyaminomethane or THAM), 2-amino-2-ethyl-1,3-propanediol, etc. Because of its effectiveness availability, and cost, the THAM is particularly preferred.

By sharp contrast, it has been found that other amino alcohols such as ethanolamine, propanolamine and butanolamine which lack, 2,2-disubstitution, do not afford oxazoline products.

The formation of the novel oxazoline materials in substantial yield, can be effected by adding from one to four moles of the aforesaid 2,2-disubstituted-2-amino-1-alkanol per mole of the thio-bis-(acylating reagent) with or without an inert diluent, and heating the mixture at 100°–240° C., preferably 170°–220° C. until reaction is complete by infrared analysis of the product showing maximal absorption for oxazoline and/or until evolution of water ceases.

Although not necessary, the presence of small amounts such as 0.01 to 2 wt.%, preferably 0.1 to 1 wt.%, based on the weight of the reactants, of a metal salt can be used in the reaction mixture as a catalyst. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and depending on the metal, it may even contribute performance benefits to the oil or gasoline. This is believed to occur with the use of zinc catalysts in lubricants.

Inert solvents which may be used in the above reaction include hydrocarbon oils, e.g. mineral lubricating oil, kerosene, neutral mineral oils, xylene, halogenated hydrocarbons, e.g., carbon tetrachloride, dichlorobenzene, tetrahydrofuran, etc.

Metal salts that may be used as catalysts in the invention include carboxylic acid salts of Zn, Co, Mn and Fe. Metal catalysts derived from strong acids (HCl, sulfonic acid, $H_2SO_4$, $HNO_3$, etc.) and bases, tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$ acids, such as the saturated or unsaturated mono- and dicarboxylic aliphatic hydrocarbon acids, particularly fatty acids. Specific examples of such desired carboxylic acid salts include zinc acetate, zinc formate, zinc propionate, zinc stearate, manganese(ous) acetate, iron tartrate, cobalt(ous) acetate, etc. Completion of the oxazoline reaction can be readily ascertained by using periodic infrared spectral analysis for maximal oxazoline formation ($C=N$ absorption band at 6.0 microns) and/or by the cessation of water evoolution.

In another embodiment of the invention the thiobis-(acylating reagent) is treated with less than a stoichiometric quantity, i.e. less than four molar equivalents e.g. 1 to 3, preferably 2 to 3, molar equivalents of THAM, to provide oxazoline-ester dispersants which are useful in themselves or can be converted to other classes of novel dispersants by treatment with polyamines to form oxazoline imide/amide products or reaction with polyols, such as pentaerythritol, preferably using ratios of 1 molar equivalent of said oxazoline-ester dispersant per 1 to 2 molar equivalents of pentaerythritol, to form novel oxazoline polyol dispersants and if desired finally reacted with alkylene oxides to form alkoxylated derivatives thereof having wide utility as additives.

It is to be understood that the oxazoline products of the invention can be both molybdated with molybdenum to enhance their lubricity activity and borated with boron to enhance the additives' anticorrosion and/or varnish inhibition activities.

"Thio" as the term is generically used in this disclosure encompasses sulfur and its congenor, i.e. selenium.

The oil-soluble oxazoline reaction products of the invention can be incorporated in a wide variety of oleaginous compositions. They can be used in lubricating oil compositions, such as automotive crankcase lubricating oils, automatic transmission fluids, etc., in concentrations generally within the range of about 0.01 to 20 wt.%, e.g. 0.1 to 10 weight percent, preferably 0.3 to 3.0 weight percent, of the total composition. The lubricants to which the oxazoline products can be added include not only hydrocarbon oils derived from petroleum but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergent and antirust properties in petroleum fuels, such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers or in turbine oils, about 0.001 to 2 wt.% will generally be used.

The additive may be conveniently dispensed as a concentrate comprising 20 to 90 parts, preferably 30 to 60, parts by weight, of the additive dissolved in a mineral lubricating oil.

EXAMPLE 1

Dithio-bis-[polyisobutenyl-bis-(5,5,-bis-methylol-2-oxazoline)]

Two-hundred grams (ca 0.154 mole) of a polyisobutenyl succinic anhydride (prepared via the reaction of polyisobutene and maleic anhydride) having a $(\overline{M}_n)$ of 1300 and a Saponification Number of 72, were diluted with 100 ml of methylene chloride and stirred at room temperature under a nitrogen blanket. Then, 10.4 g (ca 0.077 mole) of $S_2Cl_2$ were added dropwise for a period of half an hour. The reaction mixture was stirred at room temperature for about ten hours.

One-half of this product was evaporated and the residue was sparged with nitrogen at 150° C. for four hours. The resulting dithio-bis-(polyisobutenyl succinic anhydride) adduct analyzed for 2.08 wt.% S and 0.15 wt.% Cl.

About 21 g (ca 0.007 moles) of said adduct were diluted with an equal weight of mineral oil (Solvent 150 Neutral) and heated to 120° C. Then 0.1 g of zinc acetate and 3.4 g (0.028 mole) of THAM were added. The reaction mixture was heated to 180° C. for 2 hours while sparging with nitrogen and filtered. The oil solution analyzed for 0.9 wt.% nitrogen. The infrared analysis confirmed the presence of the above-identified tetraoxazoline product.

EXAMPLE 2

Dithio-bis-[polyisobutenyl-bis-(5,5-bis-methylol-2-oxazoline]

30 g (ca 0.014 mole) of a dithio-bis-(polyisobutenyl succinic anhydride) adduct derived from a polyisobutenyl succinic anhydride of $(\overline{M}_n)$ of 990 and a Sap. No. 107 and $S_2Cl_2$ were diluted with 32 g of mineral oil (Solvent 150 Neutral) and heated to 120° C. Then 0.1 g of zinc diacetate and 6.9 g (ca 0.057 moles) of THAM were added. The reaction mixture was heated to 180° C. for two hours with nitrogen sparging and then filtered. The oil solution of the oxazoline product analyzed for 1.07 wt.% nitrogen.

EXAMPLE 3

Thio-bis-[polyisobutenyl-bis-(5,5-bis-methylol-2-oxazoline)]

Five-hundred grams (ca 0.385 moles) of polyisobutenylsuccinic anhydride having a $(\overline{M}_n)$ of 775 and a Sap. No. of 84 were dissolved in 60 ml of methylene chloride and cooled to 0° C. While stirring at 0° C. under a nitrogen atmosphere, 19.8 g (ca 0.192 mole) of $SCl_2$ were added dropwise for a period of half hour. The reaction mixture was allowed to warm up to room temperature and stirred for about ten hours.

One-half of this adduct product was dehydrohalogenated by rotoevaporation under high vacuum for 6 hours at about 100° C.

The adduct analyzed for 1.34 wt.% S and 0.70 wt.% Cl. The infrared analysis was consistent with that of a thio-bis (polyisobutenylsuccinic anhydride) adduct.

About 80 g (ca 0.03 moles) of said adduct were diluted with an equal amount of mineral oil (Solvent 150 Neutral) and heated to 130° C. Then 0.1 g of zinc acetate dihydrate were added, followed by the addition of 14.5 g (ca 0.12 moles) of THAM. The reaction mixture was heated slowly to 180° C. and kept at this temperature for 2 hours while sparged with nitrogen. The oil solution was filtered and the filtrate analyzed for 1.27 wt.% nitrogen. An infrared spectrum of this product confirmed the presence of the above-identified the tetraoxazoline.

EXAMPLE 4

Dithio-bis-[polyisobutenyl-bis-(5,5-bis-methylol-2-oxazoline)]

Five hundred grams (ca 0.385 moles) of the polyisobutylene succinic anhydride used in Example 3 were dissolved in 60 ml of methylene chloride and cooled to 0° C. While stirring at 0° C. under a nitrogen blanket, 26 g (ca 0.192 moles) of sulfur monochloride were added dropwise for a period of half hour. The reaction mixture was allowed to warm up to room temperature and stirred for about ten hours.

One-half of this product was rotoevaporated under high vacuum at 100° C. for 6 hours. The resulting adduct analyzed for 2.43 wt.% S and 0.65 wt.% Cl.

Approximately 50 g (ca 0.02 moles) of the dithio-bis-(polyisobutenyl succinic anhydride) adduct were mixed with 0.1 g of zinc diacetate and diluted with an equal amount of mineral oil (Solvent 150 Neutral). The oil solution was heated to 120° C. and 9.7 g (ca 0.08 mole) of THAM were added. The reaction temperature was slowly raised to 180° C. and kept at this temperature for two hours. At the end of the second hour the oil solution was filtered. The filtrate analyzed for 1.14 wt.% nitrogen. The infrared analysis featured strong absorption band at 6.0–6.05 microns confirming the presence of an oxazoline reaction product.

EXAMPLE 5

Reaction product of 1 molar equivalent of thio-bis-adduct with 2 molar equivalents of THAM About 108 g (0.04 mole) of the thio-bis (polyisobutenylsuccinic anhydride) adduct of Example 3 was reacted with 9.7 g (0.08 mole) of THAM under the same conditions as described in Example 3. The product analyzed for 0.63 wt.% nitrogen and 1.36% sulfur.

EXAMPLE 6

Reaction product of 1 molar equivalent of thio-bis-adduct with 3 molar equivalents of THAM.

About 108 g (0.04 mole) of the adduct of Example 3 was reacted with 14.5 g (0.12 mole) of THAM under the same conditions described in Example 3. The product analyzed for 0.94 wt.% nitrogen and 1.18% sulfur.

EXAMPLE 7

Reaction product of 1 molar equivalent of thio-bis-adduct with 1 molar equivalent of THAM and then reacted with 2 molar equivalents pentaerythritol.

About 108 g (0.04 mole) of the adduct of Example 3 was reacted with 4.8 (0.04 mole) of THAM under the same conditions described in Example 3. The product analyzed for 0.41 wt.% nitrogen and 1.36% sulfur.

About 56 g (0.02 mole) of this product dissolved in 54 g of Solvent 150 Neutral Base oil, was reacted with 5.4 g (0.04 mole) of pentaerythritol (PE) by heating at 210° C. for 2 hours while passing nitrogen through the mixture. The reaction product was then purged with nitrogen for ½ hour, filtered and recovered. The product analyzed for 0.43 wt.% nitrogen and 1.23 wt.% sulfur; some unreacted PE was recovered.

EXAMPLE 8

One molar-equivalent of the 1:2 product of Example 5 was reacted with 2 molar equivalents of PE using the procedure of Example 7; the product contained 0.73 wt.% nitrogen and 1.28 wt.% sulfur.

EXAMPLE 9

Sludge Inhibition Bench (SIB) Test

The product of Examples 1, 3 and 4 to 8 and two other dispersant additives were subjected to a Sludge Inhibition Bench (SIB) Test which has been found after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling the taxicab crankcase at 1000–2000 mile intervals.

The Sludge Inhibition Bench Test is conducted in the following manner. The aforesaid used crankcase oil, which is milky brown in color, is freed of sludge by centrifuging for ½ hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5, 1.0 or 1.5 weight percent, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

VARNISH INHIBITION BENCH (VIB) TEST

In this (VIB) test each test sample consisted of 10 grams of lubricating oil containing 0.07 of a gram of the additive concentrate (50% active) which results in a total of 0.35 wt.% additive present in the test sample. The test oil to which the additive is admixed was 9.93 grams of a commercial lubricating oil obtained from a taxi after 2,000 miles of driving with said lubricating oil. Each ten gram sample was heat soaked overnight at about 140° C. and thereafter centrifuged to remove the sludge. The supernatant fluid of each sample was subjected to heat cycling from about 150° C. to room temperature over a period of 3.5 hours at a frequency of about 2 cycles per minute. During the heating phase, the gas containing a mixture of about 0.7 volume percent $SO_2$, 1.4 volume percent NO and balance air was bubbled through the test samples and during the cooling phase water vapor was bubbled through the test samples. At the end of the test period, which testing cycle can be repeated as necessary to determine the inhibiting effect of any additive, the wall surface of the test flasks in which the samples were contained are visually evaluated. Flasks in which the samples were contained are visually evaluated as to the varnish inhibition. The amount of varnish imposed on the walls is rated at values of from 1 to 7 with the higher number being the greater amount of varnish. It has been found that this test correlates with the varnish results obtained as a consequence of carrying out an MS-VC engine test.

Using the above-described tests, the dispersant action of the oxazoline additives of the present invention were compared with the dispersing power of one commercial dispersant referred to as PIBSA/TEPA. The PIBSA/TEPA was prepared by reaction of 1 mole of tetraethylene pentamine with about 2 moles of polyisobutenyl succinic anhydride obtained from polyisobutylene of about 1000 number average molecular weight. The PIBSA/TEPA dispersants each used the form of an additive concentrate containing about 50 wt.% PIBSA/TEPA in 50 wt.% mineral lubricating oil.

In addition, the oxazoline product of the present invention was also compared with polyisobutenylsuccinic anhydride-bisoxazoline material prepared in accordance with the teachings of DOS No. 2512201 in the Sludge Inhibition Bench Test. The bisoxazoline designated PIBSA/bis-oxazoline dispersant was prepared via the reaction of 2 molar proportions of tris-(hydroxymethyl) aminomethane with polyisobutenylsuccinic anhydride according to the procedure specified in this patent specification. The test results are given in Table I below.

TABLE I

| Additive | wt. % N | Mg Sludge/10g Oil at 0.5 wt. % | VIB Test Rating |
|---|---|---|---|
| Blank | — | 20.2 | 11 |
| PIBSA/TEPA | 1.5-1.6 | 9.8 | 7 |
| PIBSA/bis-oxazoline | 1.0 | 11.9 | 7 |
| Example 1 | 0.9 | 2.0 | 5 |
| Example 3 | 1.27 | 10.4 | 6 |
| Example 4 | 1.14 | 8.8 | 7 |
| Example 5 | 0.63 | 13.8 | 6 |
| Example 6 | 0.94 | 10.4 | 5 |
| Example 7 | 0.43 | 14.8 | 6.5 |
| Example 8 | 0.73 | 13.2 | 6 |

The data of Table I illustrates the superior dispersancy and/or varnish-inhibition activity of the additive products of the invention when compared with commercial dispersants known as PIBSA/TEPA and PIBSA/bis-oxazoline.

EXAMPLE 10

The sulfur-bridged products of the present invention and a commercial dispersant additive diluted in mineral oil were evaluated by thermogravimetric analysis (TGA) for evidence of thermal stability under oxidative conditions provided by air flow across each sample heated linearly from about 50° C. to 450° C. at a rate of 20°/min. Each sample of 5-8 mg (as a Solvent 150 N mineral oil solution containing 50 wt.% of an additive) in a platinum planchette was continuously weighed and recorded as the temperature was programmed upwardly at a linear rate to provide a record of sample weight loss versus temperature. The results are found in Table II.

TABLE II

| Product Additive Tested | Temperature at which the indicated percentage weight loss occurred | | | |
|---|---|---|---|---|
| | 10 Wt. % °C. | 50 Wt. % °C. | 70 Wt. % °C. | 90 Wt. % °C. |
| Solvent 150 Mineral Oil | 230 | 283 | 295 | 310 |
| Ex. 1 | 275 | 365 | 410 | 440 |
| Ex. 3 | 270 | 370 | 410 | 440 |
| Ex. 4 | 275 | 375 | 410 | 440 |
| PIBSA/bis-oxazoline | 235 | 330 | 400 | 430 |

The TGA data shown in Table II reveal that the compositions of the present invention are significantly more stable towards heat and oxidation than the reference commercial oxazoline dispersant. In addition, the TGA data show that the tetraoxazolines of the present invention tend to stabilize the base oil, e.g. S-150 N base stock oil, towards of thermal oxidative degradation. Thus, the novel structural features built into the present dispersants endow these additives with enhanced thermal stability as well as the ability to inhibit oxidation of the base stock oil. It is believed that these inhibitor properties can be related in part to the presence of sulfide functionality present in the additive molecules of the present invention.

What we claim is:

1. A process comprising the step of reacting one molar proportion of an acylating reagent of the formula

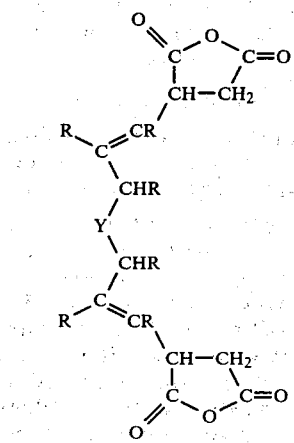

where Y is sulfur or selenium and R is hydrogen or an alkyl radical containing from 1 to 400 carbons, with from 1 to 4 molar proportions of a 2,2-disubstituted-2-amino-1-alkanol containing a total of 4 to 8 carbon atoms represented by the formula:

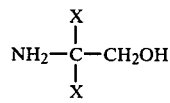

wherein X is an alkyl or hydroxyalkyl group, with at least one of the X substituents being a hydroxy alkyl group of the structure—$(CH_2)_nOH$, wherein n is 1 to 3, until the reaction product shows maximal absorption for oxazoline as measured by infrared analysis.

2. The process according to claim 1 wherein said acylating reagent is thio-bis-(polyisobutenylsuccinic anhydride) and said alkanol is thris (hydroxymethyl) amino-methane.

3. The process according to claims 1 or 2 wherein 4 molar proportions of said alkanol are reacted with one molar proportion of said acylating agent.

4. The process according to claim 1 or 2, wherein 2 to 3 molar proportions of said alkanol are reacted with 1 molar proportion of said acylating agent and said reaction product is then reacted with polyamines and/or polyols in an amount sufficient to react with the remaining carboxyl groups of said acylating agent.

5. The process according to claim 4 wherein said alkanol is tris (hydroxymethyl) amino-methane and said polyol is pentaerythritol.

6. A thio-ether reaction product prepared by the reaction of one molar proportion of thio-bis-(acylating reagent) with from 1 to 4 molar proportions of a 2,2-disubstituted-2-amino-1-alkanol at a temperature of from 100° to 240° C. until the reaction is complete by infrared analysis of the reaction product of the reaction showing maximum absorption for oxazoline.

7. A thio-ether reaction product according to claim 6 wherein said alkanol is tris (hydroxymethyl) amino-methane.

8. A thio-ether reaction product according to claim 6 or 7 wherein said alkanol is used in an amount ranging from 1 to 3 molar proportions and said reaction product is thereafter reacted with polyamines and/or polyols in an amount sufficient to react with the remaining carboxyl groups of said acylating reagent.

9. A compound represented by the formula:

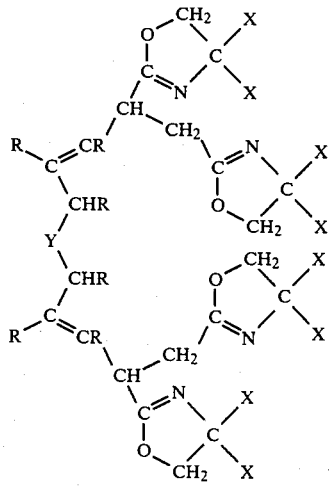

wherein R is selected from the group consisting of hydrogen and alkyl radicals containing from 1 to 400 carbons, X is selected from the group consisting of an alkyl or hydroxy alkyl group and at least one of the X substituents being a hydroxy alkyl group of the structure —$(CH_2)_nOH$ where n is 1 to 3, and Y is selected from the group consisting of —S—, —S—S—, $>S=O$, $>SO_2$, —Se— and —S—$(CH_2)_z$—S— wherein z is a number from 2 to 10.

10. A compound according to claim 9 wherein both of said X substituents are a hydroxy alkyl group of the structure —$(CH_2)_nOH$, n is 1 and Y is selected from —S— and —S—S— whereby a thio-bis (hydrocarbon-bisoxazoline) is realized.

11. Dithio-bis-[polyisobutenyl-bis-(5,5,-bis-methylol-2-oxazoline)].

12. Thio-bis-[polyisobutenyl-bis-(5,5,-bis-methylol-2-oxazoline)].

13. A composition comprising an oleaginous material of the class consisting of fuels and lubricants and at least a corrosion-inhibiting amount of a compound represented by the formula:

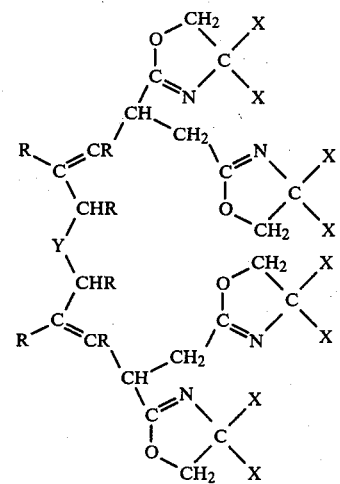

wherein R is selected from the group consisting of hydrogen and alkyl radicals containing from 1 to 400 carbons, X is selected from the group consisting of an alkyl or hydroxy alkyl group and at least one of the X substituents being a hydroxy alkyl group of the structure —$(CH_2)_nOH$ where n is 1 to 3, and Y is selected from the group consisting of —S—, —S—S—, $>S=O$, $>SO_2$, —Se— and —S—$(CH_2)_z$—S— wherein z is a number from 2 to 10.

14. A composition according to claim 13 wherein said oleaginous material is a lubricating mineral oil containing 0.01 to 20 wt.% of said compound.

15. A composition according to claim 13 wherein said oleaginous material is a lubricating mineral oil containing from 20–90 wt.% of said compound.

16. A composition according to claim 13 wherein said oleaginous material is gasoline and said compound is present in amount ranging from 4–20 parts per million based on the total weight of said composition.

* * * * *